United States Patent [19]

Beard

[11] Patent Number: 5,267,565
[45] Date of Patent: Dec. 7, 1993

[54] METHOD AND APPARATUS FOR DETERMINING THE PATENCY OF A BLOOD VESSEL

[76] Inventor: Jonathan D. Beard, Department of Surgery, Clinical Science Building, Leicester Royal Infirmary, Leicester. LE2 7LX, United Kingdom

[21] Appl. No.: 866,257

[22] Filed: Apr. 10, 1992

Related U.S. Application Data

[63] Continuation of Ser. No. 726,737, Jul. 2, 1991, abandoned, which is a continuation of Ser. No. 424,285, Nov. 20, 1989, abandoned.

[30] Foreign Application Priority Data

Feb. 18, 1988 [GB] United Kingdom ............... 8803840

[51] Int. Cl.$^5$ .............................................. A61B 5/00
[52] U.S. Cl. ............................. 128/661.08; 128/668; 128/691; 128/687
[58] Field of Search ............ 128/661.08, 661.09, 128/661.1, 662.01, 668, 677, 680–682, 687, 689, 691

[56] References Cited

U.S. PATENT DOCUMENTS

| | | | |
|---|---|---|---|
| 4,425,922 | 1/1984 | Conti et al. | 128/691 |
| 4,566,462 | 1/1986 | Janssen | 128/677 |
| 4,653,506 | 3/1987 | Romanovskaya | 128/677 |
| 4,677,983 | 7/1987 | Yamaguchi et al. | 128/680 |
| 4,777,959 | 10/1988 | Wallach et al. | 128/677 |
| 4,870,973 | 10/1989 | Ueno | 128/680 |
| 4,962,764 | 10/1990 | Matsumura | 128/691 |

FOREIGN PATENT DOCUMENTS

| | | |
|---|---|---|
| 0016399 | 10/1980 | European Pat. Off. |
| 0041696 | 12/1981 | European Pat. Off. |
| 0321717 | 6/1989 | European Pat. Off. ....... 128/661.08 |
| 2641498 | 3/1977 | Fed. Rep. of Germany ..................... 128/662.01 |

OTHER PUBLICATIONS

Experience with Atramatic vascular diagnosis with the aid of the Ultrasonic doppler technique, Electromedia, No. 2, pp. 43–48, 1976 Kratzenstein.
Instrumentation and examination procedures for a clinical vascular laboratory, Buckley et al., Medical Instrumentation, vol. 9, No. 4, 1975, pp. 181–184.
*Cardiovascular Physiology*, 2nd Edition, Berne et al., ©1972, pp. 96–97.

*Primary Examiner*—Lee S. Cohen
*Assistant Examiner*—Robert L. Nasset, Jr.
*Attorney, Agent, or Firm*—Wegner, Cantor, Mueller & Player

[57] ABSTRACT

A method and apparatus for testing the vascular condition of a patient including applying a pulsatile waveform to a part of a patient's body, observing the resultant blood flow at a location spaced from the point of application, and comparing the observed waveform with the applied waveform. In one aspect, the method and apparatus are used to assess a patient's suitability for femorodistal by-pass surgery. In another aspect, the method and apparatus are used to determine the patency calf arteries in a patient.

17 Claims, 6 Drawing Sheets

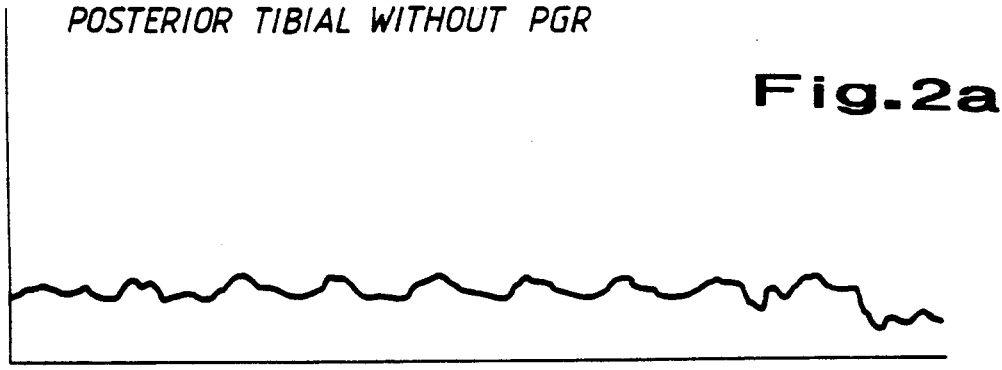
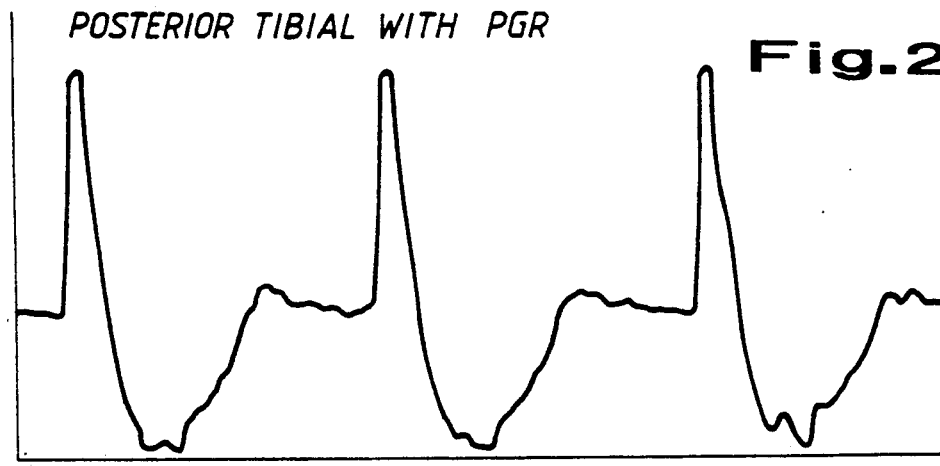
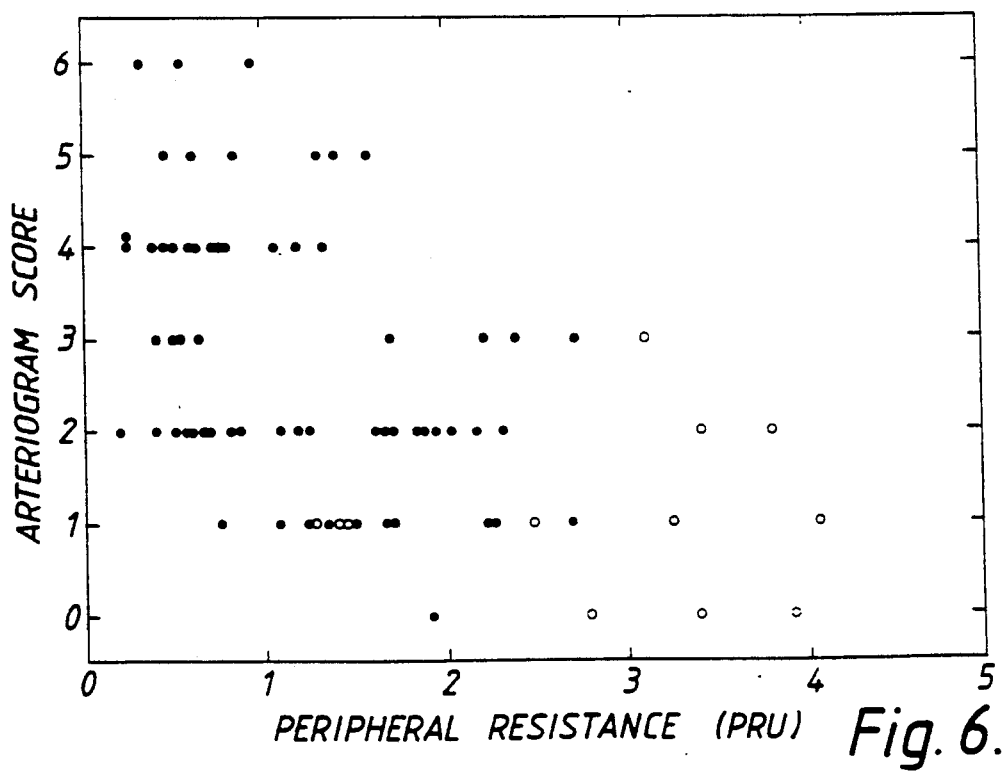

PREOPERATIVE ARTERIOGRAM SCORE VERSUS PGR SCORE.
SPEARMAN'S RANK CORRELATION, $r_s = 0.73$ $p < 0.005$.
(●=BYPASS, ○=AMPUTATION)

PGR SCORE VERSUS PERIPHERAL RESISTANCE. SPEARMAN'S
RANK CORRELATION, $r_s = -0.71$, $p < 0.005$.
(●=BYPASS ○=AMPUTATION)

METHOD AND APPARATUS FOR DETERMINING THE PATENCY OF A BLOOD VESSEL

CONTINUING DATA

This application is a continuation of U.S. application Ser. No. 07/726,737, filed Jul. 2, 1991, now abandoned, which is a continuation of U.S. application Ser. No. 07/424,285, filed Nov. 20, 1989, now abandoned.

This invention relates to medical apparatus and surgical procedures which are of particular value in connection with femorodistal, by-pass graft procedures.

BACKGROUND OF THE INVENTION

The decision to attempt a femorodistal bypass graft is usually based on the pre-operative demonstration of an adequate calf vessel runoff. It is an advantage to know the state of the runoff vessels as this may affect the level of the distal anastomosis and influence graft patency. When the popliteal artery is occluded it is essential to detect which calf vessel, if any, is patent as this will determine whether grafting is at all possible. Assessment of the pedal arch and its calf vessel connections may also influence the site of the distal anastomosis.

The recent upsurge in popularity of femorodistal grafts for limb salvage has highlighted the shortcomings of conventional pre-operative arteriography. About one-quarter of crural or pedal arteries that are judged patent on Doppler ultrasonography or direct operative exploration may fail to opacify. The use of specialized techniques such as reactive hyperaemia, vasodilators, intra-operative arteriography, or digital subtraction arteriography may increase the visualization of distal vessels but they are not always practicable or available.

Conventional pre-operative arteriography may fail to demonstrate patent calf and foot vessels, especially in the presence of severe ischaemia. Although distal vessels should be judged occluded only if there is filling of the small collaterals, this may not be achieved on the initial arteriograms. It may be uncertain whether failure to demonstrate distal vessels is due to technical factors or due to occlusion. Repeat arteriograms incur additional expense and delay with no guarantee of improved definition. Worse still, it may be assumed that vessels are occluded simply because they have not been filled with contrast medium, and the patient may thus be denied the chance of reconstruction.

Doppler ultrasonography may detect patent crural or pedal vessels that are missed on arteriography but may itself miss patent vessels because of severely damped signals due to a low perfusion pressure. Diligent searching over the area of the vessel without pressure from the probe on the skin and increasing the perfusion pressure by making the feet dependent may help, but require patience and expertise.

An ideal system for assessing distal vessel patency would be non-invasive, safe, simple and rapid to perform. Standard Doppler ultrasound is useful but may also miss patent vessels if signals are severely damped despite a meticulous technique.

SUMMARY OF THE INVENTION

A non-invasive method which may be used, inter alia, in determining calf vessel patency has now been developed. This novel method generates blood flow in patent calf arteries by means of a pulsatile cuff located about the calf of a patient. More particularly, according to one aspect of the present invention, there is provided a method of determining the patency of calf arteries in a human or non-human animal, which comprises (a) applying a series of pressure pulses to the exterior of the calf of the animal; and (b) observing blood flow at or near the level of the ankle of the animal by a non-invasive technique.

According to another aspect of the present invention, there is provided a method of testing the vascular condition of a patient, which comprises applying a pulsatile pressure waveform to a part of the patient's body and observing the resultant blood flow using a non-invasive technique at a location spaced apart from the area of application of said waveform.

Preferably, the measurement of blood flow at a point distal with respect to the location of the point of application of said pressure pulses is effected by means of a Doppler velocimeter. Preferably, the pressure pulses are applied via a cuff which is positioned around the patient's calf. The pressure pulses are advantageously produced pneumatically. Preferably the pulsatile pressure waveform has a pulse rate in the range 0.3-1.5 pulses per second. A pulse rate of 0.5-1 pulse/second is expected to be satisfactory in most cases. The magnitude of the pressure pulse preferably is in the range 150-500 nun Hg. The most advantageous pressure range is 200-300 mm Hg. The applied pressure may persist for the order of a few milliseconds before it decays to normal pressure. Such an arrangement can conveniently be achieved by using a supply of compressed gas connected to a control arrangement, e.g. a solid state pressure transducer which is used to actuate a three-way valve; one arm of the valve is connected to the source of compressed gas, the second arm is connected to the cuff, and the third arm vents to the atmosphere. The solid state pressure transducer admits gas from the source to the cuff until the pressure reaches a predetermined level, at which point the first arm (to the gas source) is closed and the third arm (which vents to the atmosphere) is put into communication with the cuff. When the pressure transducer senses that the cuff pressure has reduced to zero, it closes the vent arm and re-admits compressed gas to the cuff.

According to a second aspect of the present invention, there is provided apparatus for use in assessing the patency of blood vessels in a human or non-human animal, which apparatus comprises: (a) means for applying to the periphery of an area of the animal a pulsatile pressure wave form; and (b) means for observing the blood flow in the animal at a point distal with respect to the application of said pulsatile pressure wave form. Conveniently, the means for applying said pulsatile pressure wave form comprises (1) a source of compressed gas; (2) a pressure control system; and (3) an inflatable cuff—shaped so as to be locatable about that area of a patient (e.g. his calf) which is to be investigated. The pressure control system is preferably in the form of a pressure transducer which actuates a three-way valve, whereby compressed gas is admitted to the inflatable cuff until a predetermined pressure cut-off point is reached, whereupon the pressure transducer stops the supply of compressed gas and vents the interior of the inflatable cuff to the atmosphere; when the pressure within the inflatable cuff falls to zero (gauge), the pressure transducer closes the vent port and re-admits compressed gas to the inflatable cuff. This cycle is repeated generating thereby the pulsatile pressure wave form.

Blood flow at the distal location is preferably detected by a Doppler ultrasound technique. A conventional Doppler velocimeter (e.g. operating in the range 2 to 12 mHz) may be used for this purpose.

The apparatus and techniques described above are particularly valuable in assessing whether or not to perform a femorodistal bypass graft. If a decision to undertake this procedure is taken, it is still necessary to monitor the peripheral resistance of runoff at the beginning of the surgical procedure in order to give a more confident physiological test of runoff and to correlate with subsequent graft patency. Present methods of peripheral resistance measurement, however, are cumbersome and not well suited for clinical use.

Despite recent advances such as the use of the in situ vein technique, about one third of all femorodistal bypass grafts performed for critical ischaemia occlude within the first year, the majority within the first month. A failed graft is extremely costly in terms of increased patient morbidity, prolonged hospital stay and wasted operating time.

Continued graft patency is determined by an adequate blood flow which is largely dependent upon the state of the distal runoff vessels. Preoperative assessment is usually based upon a combination of non-invasive Doppler ankle pressures and arteriography which give little functional information and may miss patent calf vessels. Measurement of the peripheral resistance at the start of the operation has recently been claimed to provide more functional information about the runoff than is available pre-operatively.

The methods described heretofore in the literature all measure the peripheral resistance by recording the pressure generated by a constant flow of saline or blood infused into the runoff vessels. These constant-flow systems are difficult to use and time-consuming to set up. Furthermore, the constant-flow system does not correlate with natural blood flow, which varies in flow rate but more closely approximates to constant pressure flow conditions. Accordingly, another objective of the present invention was to develop a simple constant-pressure method for measuring the peripheral resistance at the start of operation.

According to a further aspect of the present invention, there is provided an infusor suitable for use in measuring peripheral resistance, which infusor comprises a first plunger arranged to act upon a syringe plunger to which the infusor is connected; and a second plunger connected to said first plunger via a compression spring. The second plunger conveniently nests into the interior of a cylindrical shaft which constitutes an extension of the first plunger; the end of said hollow cylindrical shaft can then function as a marker against a scale graduated on the cylindrical surface of the second plunger.

In use, a surgeon will connect the infusor to a disposable syringe which contains the liquid which is to be injected (preferably blood or saline), and will then use the infusor to inject the liquid into a distal artery under constant pressure conditions. This is monitored by maintaining a fixed relationship between the ends of the first and second plungers—this being readily indicated by the position of the end of the first plunger against the graduated scale provided on the shaft of the second plunger.

For a better understanding of the invention, and to show how the same may be carried into effect, reference will now be made, by way of example, to the accompany drawings, in which:

BRIEF DESCRIPTION OF THE DRAWINGS

FIGS. 2a, and b, illustrate the pulsaltile blood flow as observed by a Doppler velocimeter in the course of an assessment using the apparatus and techniques of this invention;

FIG. 6 is a plot of the pre-operative arteriogram score against the measurement of peripheral resistance at the start of the operation using the infusor of FIG. 5;

DETAILED DESCRIPTION OF THE INVENTION

In one preferred embodiment, the present invention uses a standard 10 MHz Doppler ultrasound velocimeter and a sphygmomanometer cuff driven by pulsatile compressed air. The cuff is placed around the upper calf and the pulsatile pressure generates blood flow in the calf arteries. Patent arteries can be detected by the Doppler probe at the ankle even if the existing signal is inaudible. The pedal arch patency test is also easily performed to determine continuity with the pedal arch. An occlusive thigh cuff is occasionally required to prevent interference by the normal arterial signal although it is not usually necessary in severely ischaemic limbs. Venous signals are readily differentiated from arterial ones as they are characteristically attenuated by the venous valves which prevented retrograde flow. Theoretically there might be a problem in patients with deep venous incompetence but this has not been encountered clinically.

Figure 1:
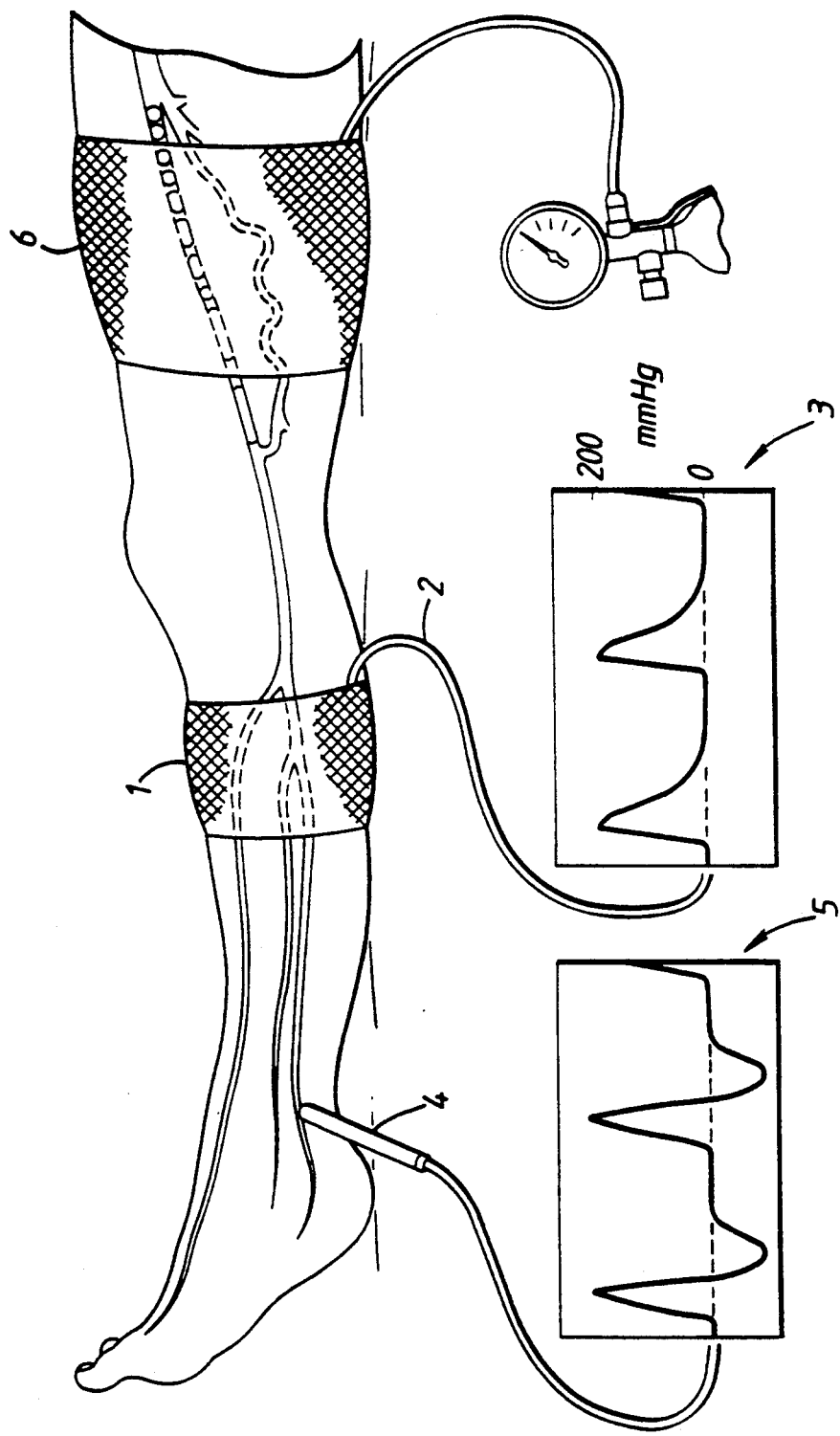
FIG. 1 illustrates the application of the invention to assessment of calf vessel patency.

Referring to FIG. 1, there is shown schematically the arrangement adopted in utilizing the PGR system described above. An inflatable cuff 1 is positioned around the patient's calf. A pulsatile pressure waveform is applied by the cuff which is fed with compressed air via a control arrangement (not shown) and supply tube 2. The pressure waveform is depicted schematically at 3, Blood flow in the runoff vessels is determined using a conventional Doppler velocimeter 4 which is held in contact with the patient's limb in the ankle region in order to detect blood flow in one of the three runoff arteries. The output of the Doppler velocimeter is illustrated at 5 (showing the signal obtained where runoff is adequate). A further cuff 6 is shown located about the patient's thigh; this functions as a conventional sphygmomanometer cuff and is required only where the normal arterial signal would interfere with that deriving from the PGR system—i.e. in patients with relatively little ischaemia.

The control unit is driven by compressed air and consists of two separate modules controlling the pulsatile and occlusive cuffs. The inflation and deflation of the pulsatile cuff is controlled by a two-way solenoid valve and an in-line solid-state pressure transducer. The pulse pressure can be varied from 0 to 300 mm Hg and the frequency of pulsation from 0 to 100/min but a standard pulse of 250 mm Hg at a rate of 50/min is usually used. The occlusive cuff pressure is controlled by a standard pressure regulator and can be varied from 0 to 300 mm Hg. For convenience, the system just described above is termed herein "pulse generated runoff" or "PGR".

Figure 8:
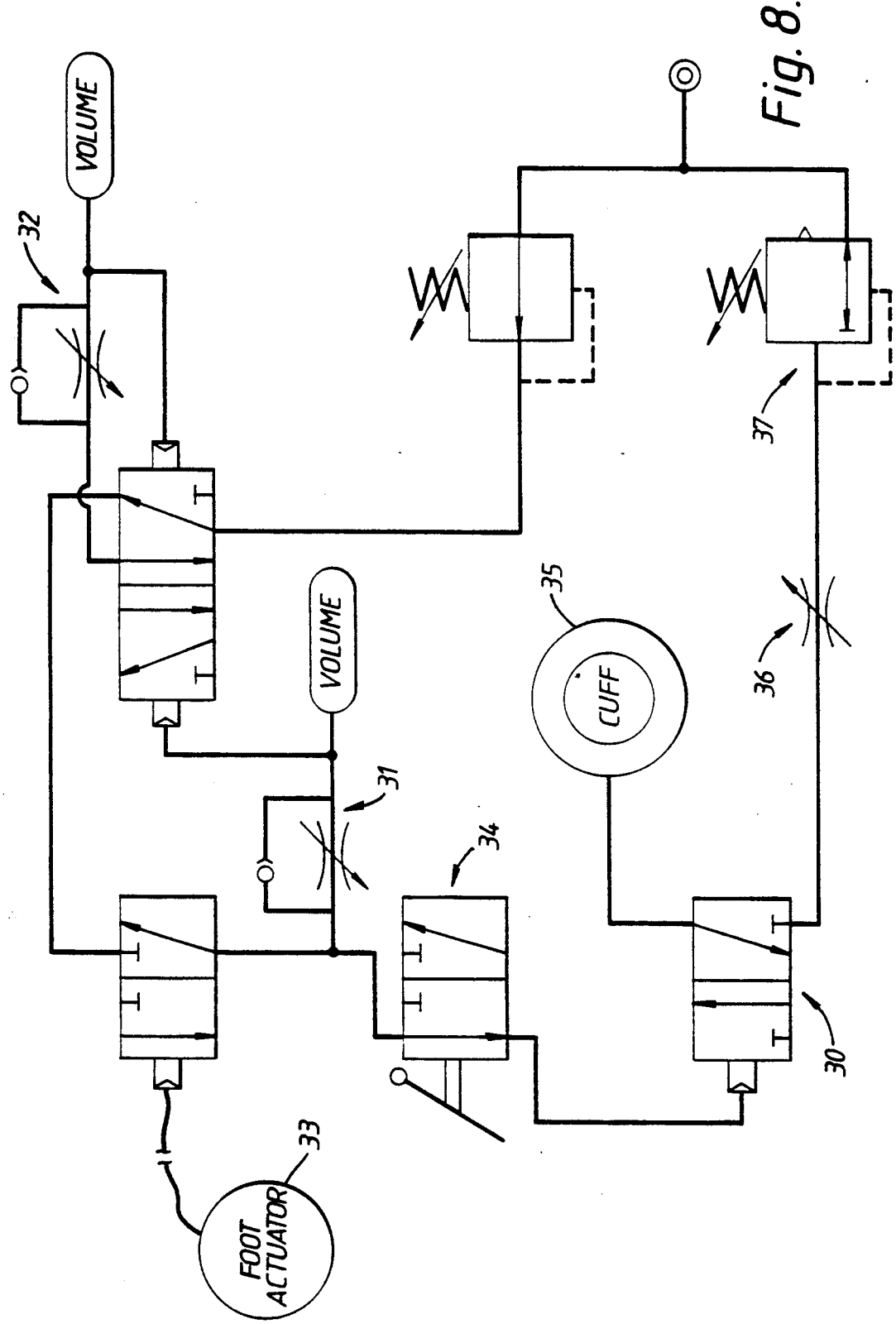
FIG. 8 is a diagram showing the pneumatic circuitry in one embodiment of this invention.
Figure 9:
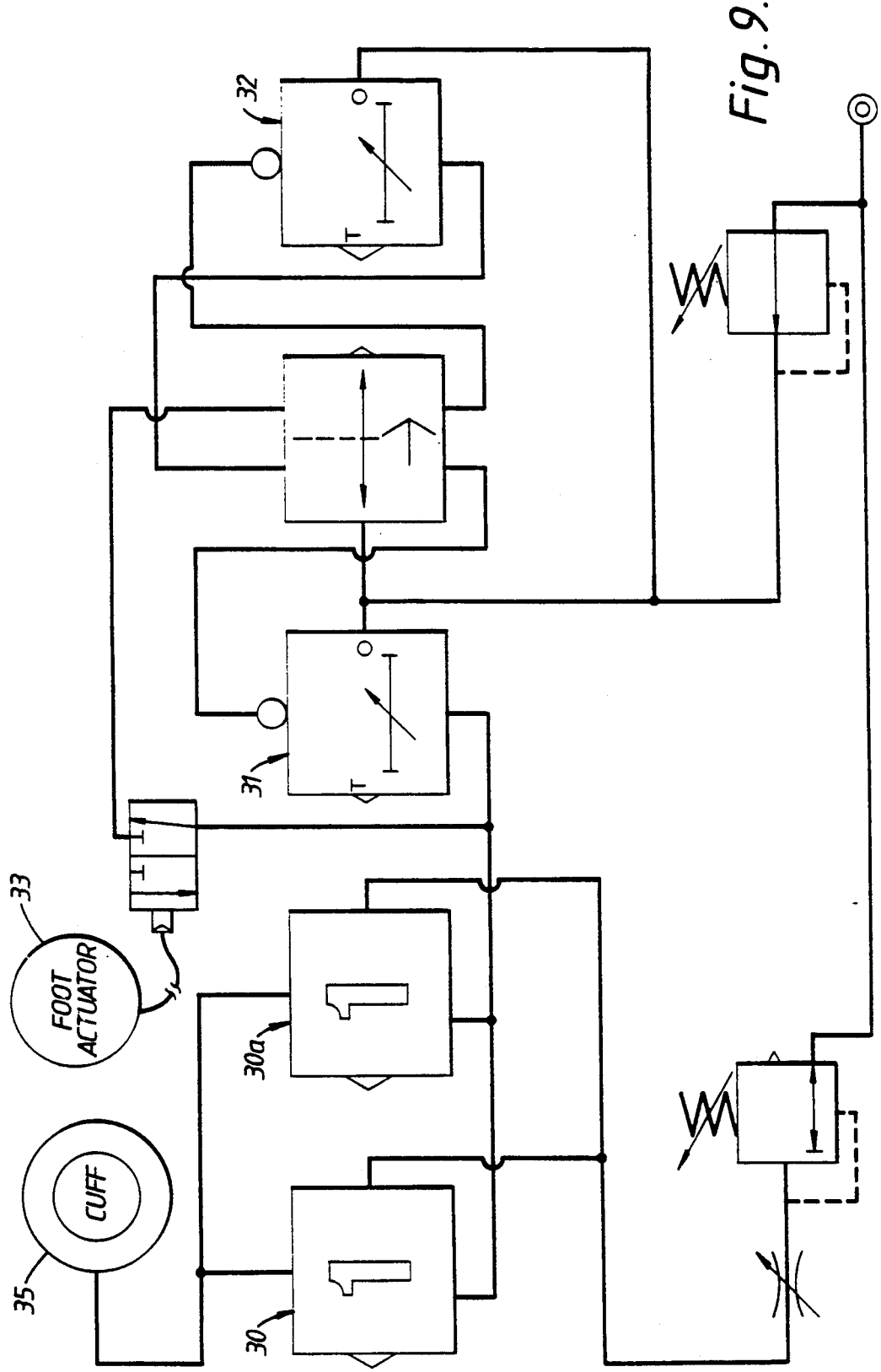
FIG. 9 is a logic circuit corresponding to the pneumatic circuitry of FIG. 8.

FIGS. 8 and 9 illustrate circuitry used in one embodiment of apparatus in accordance with this invention. Conventional symbols are used in the two circuits, to denote conventional components as will be recognized by those skilled in the art of pneumatics. The upper part of the circuit of FIG. 8 functions as a timer circuit which produces a pulse to a cuff inflate/deflate valve 30. The time in which the cuff is inflated and deflated can be adjusted by means of two throttle valves 31 and 32. The system is activated by a foot actuator 33 connected into the timer circuit in such a way that it can stop a pressure pulse activating the cuff inflate/deflate valve 30. The pressure pulse is fed to valve 30 via a two way toggle valve 34 which acts as an emergency deflate valve. Valve 30 is connected to the cuff 35 for inflation/deflation thereof. Deflation of the cuff takes place straight through valve 30 to exhaust without any throttle since it is desirable for deflation to occur as rapidly as possible. The remainder of the pneumatic circuit comprises a throttle 36 and a cuff supply regulator 37.

The logic circuit of FIG. 9 corresponds to the pneumatic circuit of FIG. 8 except that there is no emergency deflate valve 3 4 , and there are two inflate/deflate valves 30, 30a in order to provide an increased volume of air to the cuff 35.

Using the PGR system a search was made in a series of human patients for all three calf vessels at the level of the ankle (anterior tibial, posterior tibial and peroneal arteries). Each vessel was scored 2 for a normal biphasic signal, 1 for a damped monophasic signal and 0 for no signal, giving a possible total of 0–6. A normal signal has a sharp upstroke as the cuff inflates, an amplitude >2 cm and reversed flow as the cuff deflates (FIG. 2).

Preoperative arteriograms also carried out on the same group of patients, and were were scored at a weekly meeting of the consultant vascular surgeons and radiologists. Each calf vessel was scored 2 if patent to the ankle, 1 if patent but diseased and 0 if occluded, again giving a possible total of 0–6. Arteriograms were judged to be inadequate if there was no filling of calf collaterals on any of the series. Assessment of the plantar arch proved to be impossible because it was rarely adequately demonstrated.

Ninety-five ischaemic limbs with superficial femoral artery occlusion were studied in 76 patients (49 men and 27 women, aged 42–92 years, median 76 years). Of these limbs, 68 were critically ischaemic with rest pain and/or gangrene and 27 had symptoms of claudication only. All patients underwent transfemoral aortography except for six who had unilateral femoral arteriograms. Pulse-generated runoff (PGR) assessments were made on all limbs within 24 h of arteriography.

Ten control limbs were studied in five patients with isolated aortoiliac disease, whose arteriograms demonstrated three patent calf vessels down to the ankle.

The peripheral resistance was measured in all of the 62 limbs undergoing femorodistal reconstruction or amputation. Of the 62 limbs, 9 received a primary amputation based upon the pre-operative arteriogram and the degree of tissue loss. The remaining re-underwent exploration with a view to reconstruction, and of these 5 received a below-knee amputation, the other 48 receiving an in situ femorodistal vein graft. The decision to amputate was made by the consultant surgeon if the distal vessels were occluded or severely diseased. The distal anastomosis was to the infrageniculate popliteal in 29 limbs, the tibioperoneal trunk in 10 and to a calf vessel in 9 limbs.

The peripheral resistance was measured by a method similar to that described by Parvin (Br J Surg 1985; 72; 751-3). An infusion of heparinised blood was made by hand, via a soft 6 or 8 French PVC catheter inserted through an arteriotomy into the vessel chosen for the distal anastomosis. The resistance was calculated from the simultaneously recorded pressure and flow, a deduction being made for the resistance of the catheter. The resistance in the primary amputation group was measured in the calf vessel thought best on exploration before amputation. The results obtained are described below.

Figure 3:
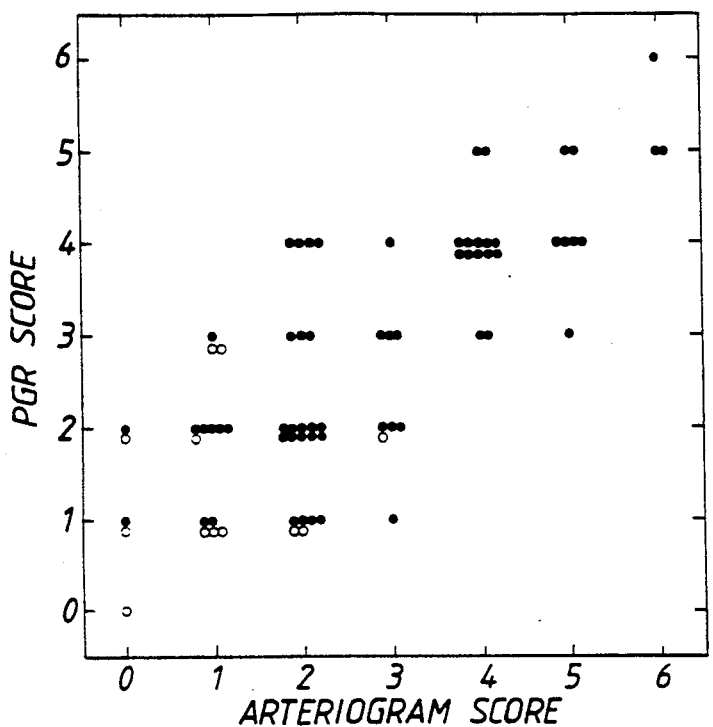
FIG. 3 is a plot showing the correlation between calf vessel patency as determined in accordance with the present invention on the one hand and as determined by arteriography on the other hand.

The 10 control limbs with arteriogram scores of 6 all scored 6 on the PGR assessment. Seventeen arteriograms (18 per cent) were judged inadequate for scoring leaving seventy-eight for comparison with the PGR (FIG. 3). There was a highly significant correlation between the arteriogram and the PGR scores (Spearman's Rank Correlation, 0.74; P<0.001). In severely ischaemic limbs the PGR tended to detect more vessels than arteriography, detecting at least one patent vessel in eight limbs (8 per cent) where no vessel was judged patent and in sixteen limbs (17 per cent) where the arteriogram was judged inadequate.

Figure 4:
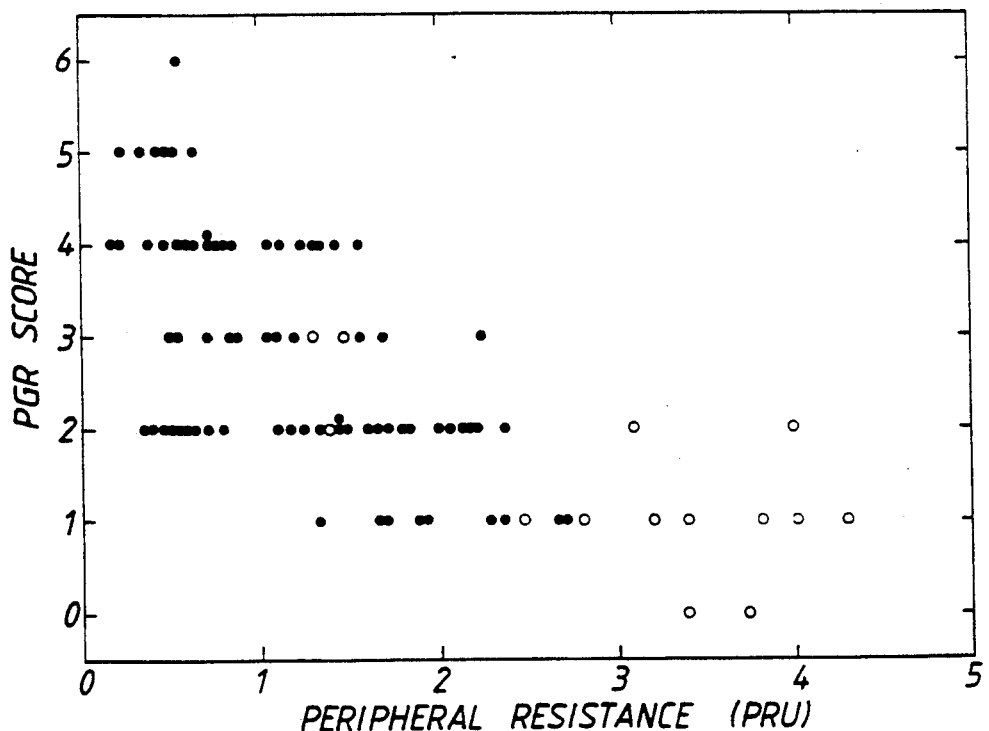
FIG. 4 is a plot of the peripheral resistance of calf vessels against the assessment of calf vessel patency as determined using apparatus and techniques in accordance with the invention.

The peripheral resistance, measured in the 62 operated limbs, correlated better with the PGR than the arteriogram score (FIG. 4) although both were highly significant (Spearman's Rank Correlation, −0.71 and −0.54 respectively; P<0.001). There was a highly significant difference between the peripheral resistance of amputated limbs and those undergoing femorodistal bypass (Mann-Whitney U test, P=0.0001). Three of the primary amputations had resistances which would have been compatible with reconstruction. No vessels were detected by pre-operative arteriography or conventional Doppler examination but the PGR system demonstrated at least one patent vessel in all three of these limbs.

It was initially thought that the PGR system worked by direct compression of the popliteal and calf arteries. However, satisfactory signals were obtained on diabetic limbs with heavily calcified incompressible vessels. This suggests that compression of the calf muscles was the source, the blood flowing retrogradely into the calf arteries. Patients did not find the pulsatile cuff unduly uncomfortable and no problems of increased ischaemia due to arterial damage were encountered.

The use of the pulse-generated runoff (PGR) system in accordance with this invention means that the distal vessels can be assessed independently of any proximal disease. Detection of patent vessels in the calf or foot is quickly and easily performed because of the enhanced flow signals.

The PGR system described above is inexpensive to construct and can be used with any available Doppler velocimeter. PGR correlates significantly with the preoperative arteriogram score but in severely ischaemic limbs may detect up to 25 per cent more patent vessels. There is a better correlation between the peripheral resistance and PGR than the arteriogram score, suggesting that PGR is a more physiological test of runoff. Pre-operative arteriography usually shows the popliteal and upper calf vessels sufficiently well to indicate the necessary level of bypass. PGR is able to confirm the patency of the distal calf and foot vessels and helps to determine the best vessel for exploration.

Although described above in relation to the assessment of arterial patency in the calf, the present invention may also be used inter alia to assess the condition of veins. For example, in healthy veins, the venous valves will prevent retrograde blood flow; hence if a Doppler velocimeter is used to assess venous flow in the technique described above, the Doppler signal will indicate whether or not there is deep venous incompetence. This condition will allow retrograde blood flow and thus will give a Doppler signal somewhat resembling that obtained with arterial measurements as described above. Where the deep veins are in a healthy condition, the Doppler signal will be strongly damped indicating the closure of the venous valves and resultant lack of retrograde blood flow.

The invention may also be used to assess the condition of the long saphenous vein prior to its use in femorodistal bypass graft surgery. If the vein is in poor condition, this will be evident as a result of examination by the technique and with the apparatus of this invention.

Furthermore, the pulsatile wave form applied by the method of this invention to a body part may be used to generate a signal from a distal blood vessel which signal is then subjected to data processing so that the invention is used to generate a transmission line analysis for blood vessels located between the point of application of the pressure wave form and the point at which blood flow measurements are taken. In this embodiment, the pulsatile pressure wave form may have a higher frequency than that used in arterial and venous assessment.

In the embodiments described above, the inflatable cuff should be of a size adequate to compress muscle within the body part about which the cuff is located. Where the pressure is derived from compressed air, the connections (e.g. tubing) between the compressed gas source and the inflatable cuff should be of wide bore in order to prevent undue pressure loss and/or pulse delays.

Figure 7:
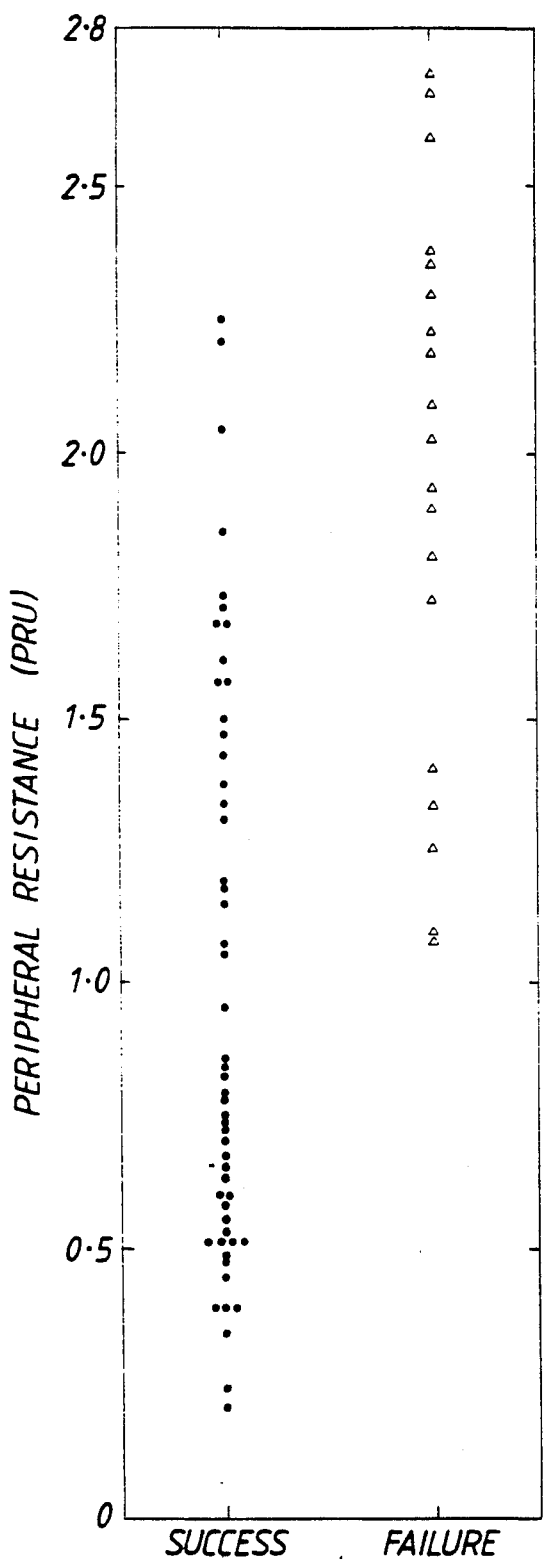
FIG. 7 is a plot of the peripheral resistance measurements versus success or failure of the femorodistal by pass grafts at one month after the operation.

A preferred embodiment of an infusor in accordance with this invention and its use in surgical procedures will now be described in greater detail with reference to FIGS. 5-7 of the drawings.

Figure 5:
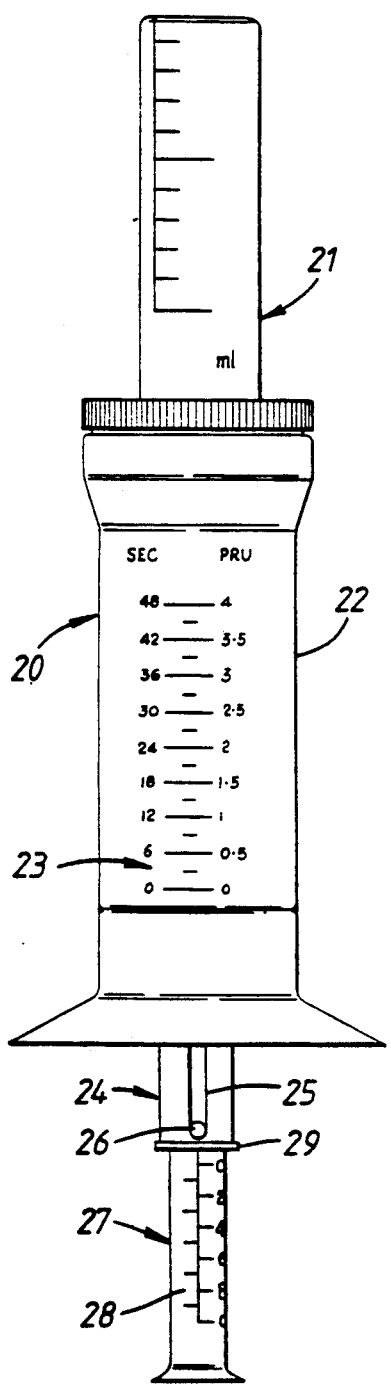
FIG. 5 is an illustration of an infusor in accordance with the invention.

Referring first to FIG. 5, an infusor 20 is shown attached to a conventional disposable syringe 21. The infusor comprises a body portion 22 which carries on its exterior surface a correlation table 23 which relates the time taken to effect an infusion (in seconds) with the peripheral resistance of the runoff. Within body portion 22 there are two concentric plungers. The first plunger acts upon the syringe 21. The distal end 24 of the first plunger includes a slot 25 which receives a pin 26 carried by the shaft 27 of the second plunger. A pressure scale 28 is provided on the side of shaft 27. Within the body of the infusor, there is a compression spring which links the action of the first and second plungers so that, under constant pressure infusion conditions, the depth of penetration of shaft 27 into the interior of part 24 of the first plunger remains constant. This is indicated by alignment of the end 29 of part 24 with the scale 28.

The plungers of the infusor shown in FIG. 5 were made of stainless steel for ease of cleaning and sterilization.

At the start of operation the artery selected for the distal anastomosis (infrageniculate popliteal or crural) was exposed and a longitudinal arteriotomy performed. An infusion of heparinized blood, at a constant pressure of 100 mmHg, was then made by hand via a soft 6 or 8 French PVC catheter (Portex) inserted into the distal vessel (FIG. 2). The patient's own blood was used for peripheral resistance measurements and was usually obtained from the femoral artery. A series of three infusions were niade and the total resistance calculated from a simple nomogram which converted the time taken to infuse 20 ml blood into peripheral resistance units (PRU):

$$\text{where } 1 \, PRU = \frac{1 \text{ mmHg blood pressure}}{1 \text{ ml/min blood flow}}$$

The lowest of the 3 measurements was used to calculate the peripheral resistance ($R_p$ by subtracting the catheter resistance ($R_C$) from the total resistance ($R_T$):

$$\text{where } R_P = R_T - R_C$$

The catheter resistance was determined by infusing blood through the catheter into a small bowl. The resistances of the 6 and 8 French catheters were about 1.75 and 0.55 PRU respectively.

Peripheral resistance measurements were made at the start of 47 in situ vein femorodistal bypass grafts performed for critical ischaemia. All patients underwent preoperative transfemoral arteriography. The anterior tibial, posterior tibial and peroneal arteries were scored at a joint weekly meeting of the consultant vascular surgeons and radiologists. Bach vessel was awarded 2 points if patent from the level of the distal anastomosis to the ankle, 1 point if patent but diseased and 0 if occluded giving a possible total of 0 to 6. The pedal circulation was often inadequately demonstrated and was not included in the scoring system.

Once the graft was completed the peripheral resistance was calculated from the graft blood flow and pressure using a newly developed Doppler flowmeter and a Gould pressure transducer. A graft was considered to be successful at 1 month if it was patent on duplex ultrasound scanning with a rise in the postoperative Doppler ankle/brachial pressure index (ABPI) of >0.25 and a clinical improvement.

The 1 month primary failure rate was 12 out of 47 (26%). The 12 failures included 8 grafts which occluded between 12 hours and 15 days postoperatively and 4 grafts which although patent, resulted in no improvement clinically or in the ABPI. The above-knees amputation rate for these failures was 55%.

The preoperative arteriograms were judged inadequate for scoring purposes in 9 cases (19%). There was a good correlation between the preoperative arteriogram score and the peripheral resistance measured at the start of operation with the constant-pressure infusor of FIG. 5 (Spearmans rank correlation), $r_s=0.85$, and this correlation is shown in FIG. 6). The peripheral resistance measured with the constant-pressure infusor correlated better than the arteriogram score with the peripheral resistance measured once the graft was completed (Spearmans rank correlation, $r_s 0.97$ and 0.86 respectively, show in FIG. 7).

There was a highly significant difference between the peripheral resistances, measured with the constant-pressure infusor, of grafts that were successful and those that failed at 1 month (Mann Whitney U test, p=0.0008). A peripheral resistance >2 PRU predicted early graft failure in 8 out of 12 cases (sensitivity 67% and specificity 89%). Although there was a significant difference between the arteriogram scores of successful and failed grafts (Mann Whitney U test, p=0.01), the predictive value was lower (sensitivity 55% and specificity 72%).

Measurement of the peripheral resistance by an infusion of saline or blood at the start of the operation is a more physiological method of assessing the runoff. Constant-flow systems may result in excessive pressure being generated if the peripheral resistance is high. This may lead to endothelial damage and falsely lower the resistance because of overdistension of the arterial system. Constant-flow systems are also expensive because of the pumps required and time-consuming to set up.

The constant-pressure infusor avoided the risk of overdistending the arterial system. It was also more physiological as the cardiovascular system depends upon a constant pressure rather than a constant flow. The constant-pressure infusor was simple to construct and easy to sterilize as it used disposable syringes. Blood rather than saline was used for the resistance measurements to avoid the need to made a correction for viscosity. Glass syringes have also been used. These have the advantage of lower friction than disposable syringes but require cleaning and sterilization.

The results confirm the findings of previous studies that measurement of the peripheral resistance before proceeding to femorodistal bypass gives more information about the runoff than preoperative arteriography. In this study a peripheral resistance of >2 PRU was associated with a very high incidence of subsequent graft failure.

Measurement of the peripheral resistance using the infusor may also have other areas of application in peripheral and coronary artery surgery. Its use after arterial embolectomy might indicate whether a successful outcome was likely or not, thus enabling other measures to be taken if necessary, e.g. thrombolytic therapy. In coronary artery bypass surgery it would be an advantage to have some indication of the likely success of a graft during the period of cardioplegia.

I claim:

1. A method of testing the vascular condition of apatient, the method comprising the steps of:
   i) selecting a portion of the body of the patient which has restricted blood flow due to a known ischaemia;
   ii) producing a pulsatile blood flow having a pulsatile waveform downstream of said portion by applying a pulsatile pressure waveform to a first part of said portion;
   iii) non-inversely observing the pulsatile waveform in the blood flow at a second part of said portion spaced apart from said first part; and
   iv) comparing the observed pulsatile waveform in the blood flow with the applied pulsatile pressure waveform.

2. A method as in claim 1, wherein said step of non-invasively observing the pulsatile waveform in the blood flow includes using Doppler untrasonography.

3. A method as in claim 1, wherein said step of producing the pulsatile pressure waveform includes pneumatically generating a pulsatile pressure waveform.

4. A method as in claim 1, wherein pulses forming said pulsatile pressure waveform have a pulse rate in the range of 0.3-1.5 pulses per second.

5. A method as in claim 4, wherein said pulses have a pulse rate in the range of 0.5-1.0 per second.

6. A method as in claim 1, wherein pulses forming said pulsatile pressure waveform have a maximum pressure in the range of 150-500 mm Hg (gauge).

7. A method as in claim 6, wherein said pulses have a maximum pressure in the range of 200-300 mm Hg (gauge).

8. A method of determining the patency of calf arteries in a human or non-human animal with restricted crural blood flow due to an ischaemia, the method comprising the steps of:
   i) producing a pulsatile blood flow having a pulsatile waveform by applying a pulsatile pressure waveform to the exterior of the calf of the animal;
   ii) non-invasively observing the pulsatile waveform in the blood flow at or near the level of the ankle of the animal;
   iii) comparing the observed pulsatile pressure waveform; and
   iv) correlating any changes between the applied pulsatile pressure waveform and the observed pulsatile waveform with the patency of the arteries.

9. A method as in claim 8, wherein said step of non-invasively observing the pulsatile waveform in the blood flow includes using Doppler ultrasonography.

10. A method as in claim 8, wherein said step of producing the pulsatile pressure waveform includes pneumatically generating a pulsatile pressure waveform.

11. A method as in claim 8, wherein pulses forming said pulsatile pressure waveform have a pulse rate in the range of 0.3-1.5 pulses per second.

12. A method as in claim 11, wherein said pulses have a pulse rate in the range of 0.5-1.0 per second.

13. A method as in claim 8, wherein pulses forming said pulsatile pressure waveform have a maximum pressure in the range of 150-500 mm Hg (gauge).

14. A method as in claim 13, wherein said pulses have a maximum pressure in the range of 200-300 mm Hg (gauge).

15. An apparatus for use in assessing the patency of blood vessels downstream from a known ischaemia in a human of non-human animal, which apparatus comprises:
   i) means for producing a pulsatile blood flow having a pulsatile waveform downstream of the ischemia by applying to the periphery of a first part of the body of said animal a pulsatile pressure waveform;
   ii) means for observing the pulsatile waveform in the blood flow at a second part of the body of said animal distal to said first part; and
   iii) means for comparing the observed pulsatile waveform in the blood flow with the applied pulsatile pressure waveform.

16. An apparatus as in claim 15, wherein said means for producing a pulsatile blood flow comprises an inflatable cuff.

17. An apparatus as in claim 16, wherein said means for producing a pulsatile blood flow comprises a pressure transducer which is arranged to actuate a three-way valve, and wherein compressed gas is introduced to said inflatable cuff until a predetermined pressure cut-off point is reached, whereupon the pressure transducer stops the supply of compressed gas and bents the interior of the inflatable cuff into the atmosphere.

* * * * *